United States Patent
Bouissou-Cadio et al.

(10) Patent No.: US 10,571,476 B2
(45) Date of Patent: Feb. 25, 2020

(54) ACTIVATORS OF TONEBP FOR USE FOR HYDRATING SKIN

(71) Applicant: CHANEL PARFUMS BEAUTE, Neuilly sur Seine (FR)

(72) Inventors: Emmanuelle Bouissou-Cadio, Clichy sous Bois (FR); Gaelle Gendronneau, Favieres (FR); Francois Lejeune, Andeville (FR); Irina Berlin, Vincennes (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 175 days.

(21) Appl. No.: 15/831,769

(22) Filed: Dec. 5, 2017

(65) Prior Publication Data
US 2018/0180629 A1    Jun. 28, 2018

(30) Foreign Application Priority Data
Dec. 28, 2016 (EP) .................................. 16306833

(51) Int. Cl.
| | | |
|---|---|---|
| G01N 33/68 | (2006.01) | |
| G01N 33/50 | (2006.01) | |
| A61K 8/9789 | (2017.01) | |
| A61Q 19/00 | (2006.01) | |

(52) U.S. Cl.
CPC ....... *G01N 33/6872* (2013.01); *A61K 8/9789* (2017.08); *A61Q 19/007* (2013.01); *G01N 33/5023* (2013.01); *G01N 33/5041* (2013.01); *G01N 33/5044* (2013.01); *G01N 33/6881* (2013.01); *G01N 2333/4703* (2013.01); *G01N 2500/04* (2013.01)

(58) Field of Classification Search
None
See application file for complete search history.

(56) References Cited

U.S. PATENT DOCUMENTS

| | | |
|---|---|---|
| 2012/0282244 A1 | 11/2012 | Maestro et al. |
| 2013/0071370 A1 | 3/2013 | Candi et al. |
| 2017/0216194 A1 | 8/2017 | Rossignol-Castera et al. |

FOREIGN PATENT DOCUMENTS

WO    2016016515 A1    2/2016

OTHER PUBLICATIONS

Al-Daraji et al. (Am J. Transl. Res. 2009 vol. 1, p. 184-202). (Year: 2009).*
Elias et al. #249 Journal of Investigative Dematology 2014 vol. 134, Suppl. 2, pp. S43. (Year: 2014).*
Taal et al. #607 in Journal of Investigative Dematology 2008 vol. 128, Suppl. 1, pp. S102. (Year: 2008).*
European Search Report, dated Mar. 29, 2017, from corresponding EP 16306833 application.
Aramburu, José, et al. "Regulation of the hypertonic stress response and other cellular functions by the Rel-like transcription factor NFAT5." Biochemical pharmacology 72.11 (2006): 1597-1604.
Cheung, Chris YK, and Ben CB Ko. "NFAT5 in cellular adaptation to hypertonic stress-regulations and functional significance." Journal of molecular signaling 8.1 (2013): 5.
Roth, Isabelle, et al. "Osmoprotective transcription factor NFAT5/TonEBP modulates nuclear factor-κB activity." Molecular biology of the cell 21.19 (2010): 3459-3474.
Warner, Ronald R., Mark C. Myers, and Dennis A. Taylor. "Electron probe analysis of human skin: determination of the water concentration profile." Journal of Investigative Dermatology 90.2 (1988): 218-224.
Caspers, Peter J., et al. "In vivo confocal Raman microspectroscopy of the skin: noninvasive determination of molecular concentration profiles." Journal of investigative dermatology 116.3 (2001): 434-442.
Schliess, Freimut, and Dieter Häussinger. "The cellular hydration state: a critical determinant for cell death and survival." Biological chemistry 383.3-4 (2002): 577-583.
Kuper, Christoph, Franz-X. Beck, and Wolfgang Neuhofer. "Osmoadaptation of Mammalian cells—an orchestrated network of protective genes." Current genomics 8.4 (2007): 209-218.
Miyakawa, Hiroshi, et al. "Tonicity-responsive enhancer binding protein, a rel-like protein that stimulates transcription in response to hypertonicity." Proceedings of the National Academy of Sciences 96.5 (1999): 2538-2542.
Woo, Seung Kyoon, et al. "TonEBP/NFAT5 stimulates transcription of HSP70 in response to hypertonicity." Molecular and cellular biology 22.16 (2002): 5753-5760.
Shim, Eun-Hee, et al. "Targeted disruption of hsp70. 1 sensitizes to osmotic stress." EMBO reports 3.9 (2002): 857-861.

* cited by examiner

*Primary Examiner* — Changhwa J Cheu
(74) *Attorney, Agent, or Firm* — Young & Thompson

(57) ABSTRACT

Disclosed are methods for screening for candidate compounds for hydrating the skin. The compounds selected according to the methods disclosed therein stimulate the intra-cellular amount and/or activity of TonEBP in keratinocytes. Preferably, the selected compounds induce a stimulation of at least 20%, preferably at least 50%, preferably at least 100% of the activity and/or intra-cellular amount of TonEBP.

6 Claims, No Drawings

ACTIVATORS OF TONEBP FOR USE FOR HYDRATING SKIN

BACKGROUND OF THE INVENTION

Field of the Invention

The invention relates to the identification and the use of compounds stimulating intra-nuclear amount or the activity of TonEBP for hydrating skin.

Osmoregulation is essential for maintaining water homeostasis in the cells. The skin approximately contains 30% of water, which contributes to its plumpness, elasticity, and resiliency. The skin consists mainly of three layers, namely, starting from the uppermost layer, the epidermis, the dermis and the hypodermis.

The epidermis comprises keratinocytes (predominantly), melanocytes (involved in pigmenting the skin) and Langerhans cells. Its function is to protect the body from the external environment and to ensure its integrity, and especially to prevent the penetration of microorganisms or chemical substances, and the evaporation of the water contained in the skin.

The epidermis is divided into four layers (strata): the stratum basale, which is the innermost layer of the epidermis, the stratum spinosum, the stratum granulosum and the stratum corneum, which is the uppermost layer of the epidermis and, accordingly, which is in direct contact with the external environment.

The epidermis, contains a gradient of water: 15% of water on the skin surface, 30% at the stratum corneum-stratum granulosum interface, (Warner et al, The Journal of investigative dermatology 1988, 20 (2) 218-224; Caspers et al, The Journal of investigative dermatology 2001 116 (3) 434-442) and finally 70% in the stratum spinosum. Perturbations in this gradient caused by internal or external factors (such as e.g. dry/humid environment or UV exposure), normally trigger the activation of adaptive responses. This may involve the upregulation of osmolyte transporters and/or osmolyte uptake to maintain cellular hydration, morphology (volume modifications) and function (Schliess and Haussinger, 2002, Biol Chem, 383, 577-83). In the absence of such adaptive mechanisms, keratinocytes may experience osmotic disequilibrium, barrier disruption and alterations in subcellular architecture (Küper et al., Curr. Genomics 2007, 8, 209-218).

These events can thus directly lead to drying of the skin and to the uncomfortable sensations of heating or redness usually appearing therewith.

Description of the Related Art

Several compositions are currently available for preventing/treating skin dehydration. However, there always remains a need to propose novel and more efficient cosmetic agents for preventing/treating skin dehydration so as reduce the sensations of cutaneous discomfort, stinging and redness caused by drying of the skin.

Surprisingly, the present inventors have demonstrated that it is possible to improve skin hydration by stimulating the activity and/or the intra-nuclear amount of the tonicity-responsive enhancer binding protein (TonEBP) in keratinocytes.

TonEBP, the only known tonicity-regulated transcription factor, is a central regulator of the osmoprotective organic osmolyte accumulation. TonEBP regulates the expression of genes involved in the production and uptake of organic osmolytes such as the sodium/myo-inositol co-transporter (SMIT), the sodium chloride/betaine co-transporter (BGT1), the sodium chloride/taurine co-transporter (TauT) and aldose reductases (AR, for biosynthesis of sorbitol) (Miyakawa et al., 1999, Proc Natl Acad Sci USA 96 (5): 2538-2542). Additionally, TonEBP induces the expression of the Hsp70 heat shock proteins, which are essential for cell survival under hypertonic stress and other osmotic stress proteins (Woo et al., Mol Cell Biol 2002, 22:5753-5760; Shim E H, EMBO Rep 2002, 3:857-861).

The activity of TonEBP induces an entry of osmolytes into the keratinocytes. Thus, to maintain a correct homeostasis, the cells will limit water efflux and/or increase water influx thereby inducing skin hydration.

Thus, the present invention provides a method for identifying useful agents for hydrating the skin, by using compounds which increase the activity and/or the intra-nuclear amount of TonEBP in the keratinocytes.

SUMMARY OF THE INVENTION

The present invention thus relates to a method for screening for candidate compounds for hydrating the skin, comprising the following steps:
 a. bringing at least one test compound into contact with a sample of keratinocytes;
 b. measuring the intra-nuclear amount or the activity of TonEBP in said keratinocytes;
 c. selecting the compounds which stimulate the intra-nuclear amount and/or activity of TonEBP in the keratinocytes treated in a. compared with untreated keratinocytes.

According to a first embodiment, step b. is performed before and after step a. In this case, the intra-nuclear amount or activity of TonEBP measured in the keratinocytes before step a. corresponds to the control value (i.e. untreated keratinocytes). Thus, step c. comprises the selection of the compounds which stimulate the expression of TonEBP in the keratinocytes treated in a. compared with the same keratinocytes before step a.

According to another embodiment, the method comprises a first step a'. of preparing samples of keratinocytes. Thus, preferably, the present invention relates to a method for screening for candidate compounds for hydrating the skin, comprising the following steps:
 a'. preparing at least two samples of keratinocytes;
 a. bringing one of the samples into contact with at least one test compound;
 b. measuring the intra-nuclear amount or the activity of TonEBP in said samples; and
 c. selecting the compounds which stimulate the intra-nuclear amount and/or activity of TonEBP in the keratinocytes treated in a. compared with the sample of untreated keratinocytes.

In this second embodiment, the intra-nuclear amount or activity of TonEBP measured in the sample of keratinocytes not submitted to step a. corresponds to the control value (i.e. untreated keratinocytes). In a particular embodiment, the compounds selected according to the methods of the present invention induce a stimulation of at least 20%, preferably at least 50%, preferably at least 100% of the activity and or intra-nuclear amount of TonEBP in the keratinocytes treated in a. compared with untreated keratinocytes.

In a particular embodiment, the keratinocytes used for performing the method according to the present invention are osmostressed keratinocytes.

In the context of the present invention, "hydrating the skin", means maintaining the natural humidity of the skin and preventing its drying.

"TonEBP", also referred to as "the tonicity-regulated transcription factor" or the "nuclear factor of activated T-cells 5" (NFAT5), is a member of the nuclear factors of activated T cells (NFAT) family of transcription factors. It is encoded by the NFTA5 gene which is available under the reference ENSG00000102908 in the Ensembl Gene Database. TonEBP stimulates the transcription of genes coding for aldose reductase (AR), the sodium chloride-betaine co-transporter (BGT1, SLC6A12), the sodium/myo-inositol co-transporter (SMIT, SLC5A3), the taurine transporter (TauT, SLC6A6) and neuropathy target esterase which are involved in the production and uptake of organic osmolytes.

The test compounds tested may be of any type. They may be of natural origin or may have been produced by chemical synthesis. This may involve a library of structurally defined chemical compounds, uncharacterized compounds or substances, or a mixture of compounds.

Natural compounds include compounds from vegetal origin, like plants. Preferably, the test compounds are vegetal, preferably chosen from botanical extracts.

According to step a., the test compound is put into contact with a sample of keratinocytes.

According to step b., the intra-nuclear amount and/or the activity of TonEBP is measured in said keratinocytes.

The "intra-nuclear amount of TonEBP" refers to the amount of TonEBP in the nucleus of the keratinocyte. The skilled person knows several techniques for measuring the intra-nuclear amount of TonEBP. Such techniques include for instance immunofluorescence techniques or fluorescent-protein tagging.

The term "activity of TonEBP" is intended to mean the ability of TonEBP to regulate cell volume upon osmotic stress. Said activity can e.g. be evaluated by determining the transcription level of the genes to which TonEBP it hybridizes (such as genes SLC6A12, SLC5A3, SLC6A6). Those skilled in the art are familiar with the techniques for measuring the transcription level of genes to which TonEBP hybridizes. Techniques based on hybridization of the sequence with specific nucleotide probes are the most common, like Northern blotting, RT-PCR (reverse transcriptase polymerase chain reaction), quantitative RT-PCR (qRT-PCR). Western blot can also be used for evaluating the level of the proteins whose expressions are regulated by TonEBP.

The intra-nuclear amount or activity of TonEBP after treatment with the test compound is then compared to a control value, i.e. a value obtained in the same keratinocytes before treatment, or a value obtained in another sample of keratinocytes which are untreated.

In a particular embodiment, the useful compounds are those for which a stimulation of at least 20%, preferably at least 50%, preferably at least 100% of the activity and/or of the intra-nuclear amount of TonEBP is measured in the treated keratinocytes compared with untreated keratinocytes.

The compounds selected by means of the screening methods defined herein can subsequently be tested on other in vitro models and/or in vivo models (in animals or humans) for their effects on skin hydration. Compounds which are selected according to the present invention are "activators" of TonEBP.

A subject of the invention is also a non-therapeutic use of an activator of TonEBP, said activator being identified according to the above described method, for hydrating the skin. A "non-therapeutic use" is e.g. a cosmetic use.

According to another aspect, an object of the present invention is the use of at least one TonEBP activator, said activator being identified according to the above described method, to make a therapeutic composition for hydrating the skin. The present invention thus also relates to a TonEBP activator which has been identified according to the above described method, for use in a therapeutic method for hydrating the skin.

The activator refers to a compound which substantially increases the intra-nuclear amount and/or activity of TonEBP. The term "substantially" signifies an increase of at least 20%, preferably at least 50%, preferably at least 100%.

The TonEBP activator can be used in a proportion of from 0.001 to 10% by weight, preferably in a proportion of from 0.01 to 5% by weight of the composition.

The TonEBP activators identified according to the screening method described above can be formulated within a composition, in combination with a physiologically acceptable carrier, preferably a cosmetically acceptable medium, i.e. a medium that is suitable for use in contact with human skin without any risk of toxicity, incompatibility, instability or allergic response and especially that does not cause any sensations of discomfort (redness, tautness, stinging, etc.) that are unacceptable to the user. These compositions may be administered, for example, orally, or topically. Preferably, the composition is applied topically. By oral administration, the composition may be in the form of tablets, gel capsules, sugar-coated tablets, syrups, suspensions, solutions, powders, granules, emulsions, suspensions of microspheres or nanospheres or lipid or polymeric vesicles for controlled release. By topical administration, the composition is more particularly for use in treating the skin and the mucous membranes and may be in the form of salves, creams, milks, ointments, powders, impregnated pads, solutions, gels, sprays, lotions or suspensions. It may also be in the form of suspensions of microspheres or nanospheres or lipid or polymeric vesicles or polymeric patches or hydrogels for controlled release. This composition for topical application may be in anhydrous form, in aqueous form or in the form of an emulsion. The composition for topical application may be in the form of an oil-in-water, water-in-oil or multiple emulsion (W/O/W or O/W/O), which may optionally be microemulsions or nanoemulsions, or in the form of an aqueous dispersion, a solution, an aqueous gel or a powder. In a preferred variant, the composition is in the form of a gel, a cream or a lotion.

The physiologically acceptable carrier of the composition generally comprises water and optionally other solvents such as ethanol.

This composition is preferably used as a care and/or cleansing product for facial and/or bodily skin and it may especially be in the form of a fluid, a gel or a mousse, conditioned, for example, in a pump-dispenser bottle, an aerosol or a tube, or in the form of cream conditioned, for example, in a jar. As a variant, it may be in the form of a makeup product and in particular a foundation or a loose or compact powder.

It may comprise various adjuvants, such as at least one compound chosen from:
  oils, which may be chosen especially from: linear or cyclic, volatile or non-volatile silicone oils, such as polydimethylsiloxanes (dimethicones), polyalkylcyclosiloxanes (cyclomethicones) and polyalkylphenylsiloxanes (phenyl dimethicones); synthetic oils such as fluoro oils, alkylbenzoates and branched hydrocarbons such as polyisobutylene; plant oils and especially soybean oil or jojoba oil; and mineral oils such as liquid petroleum jelly;

waxes such as ozokerite, polyethylene wax, beeswax or carnauba wax;

silicone elastomers obtained especially by reaction, in the presence of a catalyst, of a polysiloxane containing at least one reactive group (especially hydrogen or vinyl) and bearing at least one alkyl group (especially methyl) or phenyl, in a terminal and/or side position, with an organosilicone such as an organohydrogenopolysiloxane;

surfactants, preferably emulsifying surfactants, whether they are nonionic, anionic, cationic or amphoteric, and in particular fatty acid esters of polyols such as fatty acid esters of glycerol, fatty acid esters of sorbitan, fatty acid esters of polyethylene glycol and fatty acid esters of sucrose; fatty alkyl ethers of polyethylene glycol; alkylpolyglucosides; polysiloxane-modified polyethers; betaine and derivatives thereof; polyquaterniums; ethoxylated fatty alkyl sulfate salts; sulfosuccinates; sarcosinates; alkyl and dialkyl phosphates, and salts thereof; and fatty acid soaps;

co-surfactants such as linear fatty alcohols and in particular cetyl alcohol and stearyl alcohol;

thickeners and/or gelling agents, and in particular crosslinked or non-crosslinked, hydrophilic or amphiphilic homopolymers and copolymers, of acryloylmethylpropanesulfonic acid (AMPS) and/or of acrylamide and/or of acrylic acid and/or of acrylic acid salts or esters; xanthan gum or guar gum; cellulose derivatives; and silicone gums (dimethiconol);

organic screening agents, such as dibenzoylmethane derivatives (including butyl-methoxydibenzoylmethane), cinnamic acid derivatives (including ethylhexyl methoxycinnamate), salicylates, para-aminobenzoic acids, β,β'-diphenyl acrylates, benzophenones, benzylidenecamphor derivatives, phenylbenzimidazoles, triazines, phenylbenzotriazoles and anthranilic derivatives;

inorganic screening agents, based on mineral oxides in the form of coated or uncoated pigments or nanopigments, and in particular based on titanium dioxide or zinc oxide;

dyes;

preserving agents;

sequestrants such as EDTA salts;

fragrances;

and mixtures thereof, without this list being limiting.

Examples of such adjuvants are especially mentioned in the CTFA dictionary (International Cosmetic Ingredient Dictionary and Handbook published by The Cosmetic, Toiletry and Fragrance Association, 11th edition, 2006), which describes a wide variety, without limitation, of cosmetic and pharmaceutical ingredients usually used in the skincare industry, that are suitable for use as additional ingredients in the compositions according to the present invention.

The composition may also comprise at least one compound with an optical effect such as fillers, pigments, nacres, tensioning agents and matting polymers, and mixtures thereof.

The term "fillers" should be understood as meaning colorless or white, mineral or synthetic, lamellar or non-lamellar particles suitable for giving the composition body or rigidity and/or softness, a matt effect and uniformity immediately on application. Fillers that may especially be mentioned include talc, mica, silica, kaolin, Nylon® powders such as Nylon-12 (Orgasol® sold by the company Atochem), polyethylene powders, polyurethane powders, polystyrene powders, polyester powders, optionally modified starch, silicone resin microbeads such as those sold by the company Toshiba under the name Tospearl®, hydroxyapatite, and hollow silica microspheres (Silica Beads® from the company Maprecos).

The term "pigments" should be understood as meaning white or colored, mineral or organic particles that are insoluble in the medium, which are intended to color and/or opacify the composition. They may be of standard or nanometric size. Among the mineral pigments that may be mentioned are titanium dioxide, zirconium dioxide and cerium dioxide, and also zinc oxide, iron oxide and chromium oxide.

The term "nacres" should be understood as meaning iridescent particles that reflect light. Among the nacres that may be envisaged, mention may be made of natural mother-of-pearl, mica coated with titanium oxide, with iron oxide, with natural pigment or with bismuth oxychloride, and also colored titanium mica.

The mass concentration in the aqueous phase of these fillers and/or pigments and/or nacres is generally from 0.1% to 20% and preferably from 0.2% to 7% by weight relative to the total weight of the composition.

The term "tensioning agent" should be understood as meaning a compound suitable for making the skin taut and, by means of this tension effect, making the skin smooth and reducing or even immediately eliminating wrinkles and fine lines therefrom. Tensioning agents that may be mentioned include polymers of natural origin. The term "polymer of natural origin" means polymers of plant origin, polymers derived from integuments, egg proteins and latices of natural origin. These polymers are preferably hydrophilic. Polymers of plant origin that may especially be mentioned include proteins and protein hydrolyzates, and more particularly extracts of cereals, of legumes and of oil-yielding plants, such as extracts of corn, of rye, of wheat, of buckwheat, of sesame, of spelt, of pea, of bean, of lentil, of soybean and of lupin. The synthetic polymers are generally in the form of a latex or a pseudolatex and may be of polycondensate type or obtained by free-radical polymerization. Mention may be made especially of polyester/polyurethane and polyether/polyurethane dispersions. Preferably, the tensioning agent is a copolymer of PVP/dimethiconyl acrylate and of hydrophilic polyurethane (Aquamere S-2001® from the company Hydromer).

The term "matting polymers" means herein any polymer in solution, in dispersion or in the form of particles, which reduces the sheen of the skin and which unifies the complexion. Examples that may be mentioned include silicone elastomers; resin particles; and mixtures thereof. Examples of silicone elastomers that may be mentioned include the products sold under the name KSG® by the company Shin-Etsu, under the name Trefil®, BY29® or EPSX® by the company Dow Corning or under the name Gransil® by the company Grant Industries.

The composition used according to the invention may also comprise active agents other than the TonEBP activator, and in particular at least one active agent chosen from: agents that stimulate the production of growth factors; anti-glycation or deglycating agents; agents that increase collagen synthesis or that prevent its degradation (anti-collagenase agents and especially matrix metalloprotease inhibitors); agents that increase elastin synthesis or prevent its degradation (anti-elastase agents); agents that stimulate the synthesis of integrin or of focal adhesion constituents such as tensin; agents that increase the synthesis of glycosaminoglycans or proteoglycans or that prevent their degradation (anti-proteoglycanase agents); agents that increase fibroblast proliferation; depigmenting or anti-pigmenting agents; antioxidants or free-radical scavengers or anti-pollution agents; and mixtures thereof, without this list being limiting.

Examples of such agents are especially: plant extracts and in particular extracts of *Chondrus crispus*, of *Thermus thermophilus*, of *Pisum sativum* (Proteasyl® TP LS), of *Centella asiatica*, of Scenedesmus, of *Moringa pterygosperma*, of witch hazel, of *Castanea sativa*, of *Hibiscus sabdriffa*, of *Polianthes tuberosa*, of *Argania spinosa*, of *Aloe vera*, of *Narcissus tarzetta*, or of liquorice; an essential oil of *Citrus aurantium* (Neroli); α-hydroxy acids such as glycolic acid, lactic acid and citric acid, and esters thereof; β-hydroxy acids such as salicylic acid and derivatives thereof; plant protein hydrolyzates (especially of soybean or of hazelnut); acylated oligopeptides (sold especially by the company Sederma under the trade names Maxilip®, Matrixyl® 3000, Biopeptide® CL or Biopeptide® EL); yeast extracts and in particular of *Saccharomyces cerevisiae*; algal extracts and in particular of laminairia; vitamins and derivatives thereof such as retinyl palmitate, ascorbic acid, ascorbyl glucoside, magnesium or sodium ascorbyl phosphate, ascorbyl palmitate, ascorbyl tetraisopalmitate, ascorbyl sorbate, tocopherol, tocopheryl acetate and tocopheryl sorbate; arbutin; kojic acid; ellagic acid; and mixtures thereof.

As a variant or in addition, the composition used according to the invention may comprise at least one elastase inhibitor (anti-elastase), such as an extract of *Pisum sativum* seeds that is sold especially by the company Laboratoires Sérobiologiques/Cognis France under the trade name Proteasyl TP LS®.

The composition may also contain inert additives or combinations of these additives, such as wetting agents, stabilizers, moisture regulators, pH regulators, osmotic pressure modifiers, or UV-A and UV-B screens.

DESCRIPTION OF THE PREFERRED EMBODIMENTS

Examples

Example 1

Evaluation of TONEBP Protein Localization in Normal Human Keratinocytes Exposed to Osmotic Stress Versus Unstressed Cells The aim of the experiment is to visualize the impact of a hyperosmotic stress on the TonEBP intracellular localization and protein amount. This protocol allows visualizing the immunofluorescence signal specific for TonEBP in Normal Human Epidermal Keratinocytes (NHEK).
Material and Methods:

NHEK (Promocell) derived from two juvenile donors were cultivated in 4-well chamber slides in Keratinocyte Growth Medium (KGM2 basal medium+SupplementMix, PromoCell) at 37° C., 5% CO2. At 70% confluence, cells were washed with PBS buffer (Life Technologies) and stressed by adding 100 or 200 mM NaCl (Sigma S5150) during 6 hours. For the unstressed cells, the culture of the cells was continued in the absence of NaCl.

After stress, cells were rinsed with PBS1× buffer and fixed with 10% formalin for 15 minutes and permeabilized with Triton X-100 (0.1%) for 10 minutes. To prevent non-specific binding, goat serum 3%-PBS 1× was added at room temperature during 1 hour. Primary antibody (1/300) was added overnight at 4° C. The secondary antibody, Alexafluor 546 goat anti-Rabbit IgG (H+L), was incubated at room temperature during one hour and DAPI (Sigma 32670-25MG-F 10 mg/ml) was used to visualize the cell nucleus. Samples were mounted in special mounting media for immunofluorescence (Vectashield Vector Laboratories H-1000) and sealed with nail polish.
Results:

TonEBP protein is well detected in unstressed cells, both in nucleus and in cytoplasm. Following hyperosmotic stress treatment with NaCl at 100 or 200 mM, the TONEBP nuclear signal is increased and the cell volume reduced compared to unstressed cells (Data not shown).

Example 2

TonEBP Protein Localization/Level Assessment in Osmostressed Human Keratinocytes Following Treatment with a Botanical Extract The effect of a botanical extract Oleo Camellia Noir on the protein level and intracellular localization of TONEBP were evaluated by specific immunofluorescence staining in hyperosmo- and un-stressed conditions.

Oleo Camellia Noir extract is a botanical extract obtained from the flower of camellia japonica according to the procedure disclosed in WO 2016/016515.
Material and Methods:

NHEK (Promocell) derived from two juvenile donors were cultivated in 4-well chamber slides in Keratinocyte Growth Medium (KGM2 basal medium+SupplementMix, PromoCell) at 37° C., 5% CO2. Cells at approximately 50% confluence were pre-treated with 0.05% Oleo Camellia Noir (OA Noir) during 48 hours then 100 or 200 mM NaCl (Sigma S5150) was added during 6 hours to induce hyperosmotic stress.
Results:

Under hyperosmotic stress (NaCl 100 or 200 mM), OA Noir treated cells showed a clear increase of the TONEBP nuclear signal compared to untreated cells. OA treatment induced an increase of the cell volume in the treated cells compared to untreated cells (Data not shown).

OA treatment not only increases the TonEBP nuclear signal but it also limits its dissemination into the cytoplasm. Oleo Camelia noir treatment promotes TonEBP synthesis in response to hyperosmotic stress, thereby enhancing skin hydration.

The invention claimed is:

1. A method for screening for candidate compounds for hydrating the skin, comprising the following steps:
    a. bringing at least one test compound in contact with a sample of keratinocytes;
    b. measuring the intra-cellular amount or the activity of the tonicity-responsive enhancer binding protein (TonEBP) in said keratinocytes;
    c. selecting the compounds which substantially increase the intra-cellular amount and/or activity of TonEBP in the keratinocytes treated in a. compared with untreated keratinocytes for possible incorporation into a cosmetic composition for hydrating the skin.

2. The method according to claim 1, wherein step b. is performed before and after step a.

3. The method according to claim 1, wherein said method comprises the following steps:
    a'. preparing at least two samples of keratinocytes;
    a. bringing one of the samples into contact with at least one test compound;

b. measuring the expression or the activity of TonEBP in said samples; and c. selecting the compounds which stimulate the expression and/or activity of TonEBP in the keratinocytes treated in a. compared with the sample of untreated keratinocytes.

4. The method according to claim 1, wherein said keratinocytes are osmostressed keratinocytes.

5. The method according to claim 1, wherein the test compounds are chosen from botanical extracts.

6. The method according to claim 1, wherein the compound selected at step c. stimulates the intra-cellular amount and/or activity of TonEBP of at least 30%.

* * * * *